(12) United States Patent
Garcia Perez et al.

(10) Patent No.: US 11,052,245 B2
(45) Date of Patent: Jul. 6, 2021

(54) DEVICE AND METHOD FOR LOCALIZED DELIVERY AND EXTRACTION OF MATERIAL

(71) Applicant: Helsingin Yliopisto, Helsinki (FI)

(72) Inventors: Alejandro Garcia Perez, Helsinki (FI); Heikki Juhani Nieminen, Helsinki (FI); Aino Tietäväinen, Vantaa (FI); Edward Haeggström, Helsinki (FI)

(73) Assignee: HELSINGIN YLIOPISTO, Helsinki (FI)

( * ) Notice: Subject to any disclaimer, the term of this patent is extended or adjusted under 35 U.S.C. 154(b) by 276 days.

(21) Appl. No.: 15/748,657

(22) PCT Filed: Jul. 2, 2016

(86) PCT No.: PCT/FI2016/050488
§ 371 (c)(1),
(2) Date: Jan. 30, 2018

(87) PCT Pub. No.: WO2017/021585
PCT Pub. Date: Feb. 9, 2017

(65) Prior Publication Data
US 2018/0221656 A1    Aug. 9, 2018

(30) Foreign Application Priority Data

Aug. 4, 2015   (FI) ...................... 20155572

(51) Int. Cl.
*H02K 44/02*    (2006.01)
*A61N 1/32*     (2006.01)
(Continued)

(52) U.S. Cl.
CPC .............. *A61N 1/325* (2013.01); *A61M 5/30* (2013.01); *A61M 37/00* (2013.01); *A61N 2/002* (2013.01);
(Continued)

(58) Field of Classification Search
CPC ....... F04B 17/00; F04B 19/006; H02K 44/02; H02K 44/04; H02K 44/06; H02K 44/10
See application file for complete search history.

(56) References Cited

U.S. PATENT DOCUMENTS

| | | | | |
|---|---|---|---|---|
| 4,990,845 A | * | 2/1991 | Gord | ......................... G05F 3/24 323/312 |
| 5,056,517 A | * | 10/1991 | Fenici | .................... A61B 5/042 607/2 |

(Continued)

FOREIGN PATENT DOCUMENTS

| | | |
|---|---|---|
| WO | 96/18425 A1 | 6/1996 |
| WO | 2006/086719 A1 | 8/2006 |

OTHER PUBLICATIONS

Lashmar, U. T., Manger J., Investigation into the potential for iontophoresis facilitated transdermal delivery of acyclovir. International Journal of Pharmaceutics 1 1 1 (1) ,73-82. 06.1 0.1 994.
(Continued)

*Primary Examiner* — Philip E Stimpert
(74) *Attorney, Agent, or Firm* — Jacob Eisenberg (57) ABSTRACT

The present invention relates to a device exploiting magneto-hydrodynamics (MHD) for localized delivery of material into a target or extraction of material from a target. The device includes a frame (101) comprising a space (102) for conductive fluid and the material, at least one pair of electrodes (103A, 103B) facing each other, a source of electric current (105), a magnet (105), and an opening (106). The electric current and the magnetic field are synchronized so that the material can be moved from the volume between the electrodes through the opening towards the target or from the target through the opening towards the volume. According to the invention the volume is ≤2000 mm³, in proviso that mean distance between tips of the electrodes is ≤20 mm.

8 Claims, 9 Drawing Sheets

(51) Int. Cl.
    *F04B 19/00*      (2006.01)
    *A61M 5/30*      (2006.01)
    *F04B 17/00*      (2006.01)
    *A61M 37/00*      (2006.01)
    *A61N 2/00*      (2006.01)

(52) U.S. Cl.
    CPC ............ *F04B 17/00* (2013.01); *F04B 19/006* (2013.01); *H02K 44/02* (2013.01); *A61M 2037/0007* (2013.01)

(56) References Cited

U.S. PATENT DOCUMENTS

| | | | |
|---|---|---|---|
| 5,961,800 A * | 10/1999 | McBride | B01L 3/50273 204/450 |
| 2002/0147424 A1 | 10/2002 | Ostrow et al. | |
| 2007/0066930 A1 | 3/2007 | Tanioka | |
| 2009/0093669 A1 | 4/2009 | Farone | |
| 2010/0249488 A1 | 9/2010 | Kardos | |
| 2011/0037325 A1* | 2/2011 | Ciocanel | F04F 99/00 310/11 |

OTHER PUBLICATIONS

Murthy, S. N., Sammeta S. M., Bowers, C., Magnetophoresis for enhancing transdermaldrug delivery: Mechanistic studies and patch design. Journal of Controlled Release 1 48(2), 1 97-2A3. 01 .1 2.201 O.

* cited by examiner

DEVICE AND METHOD FOR LOCALIZED DELIVERY AND EXTRACTION OF MATERIAL

FIELD

The present invention relates to a device and a method exploiting magneto-hydrodynamics (MHD) for localized delivery of material into a target or extraction of the material from a target.

BACKGROUND

Much effort is done to develop methods and devices for localized delivery of drugs for targeted therapy. Localized drug delivery allows targeting drugs towards specific tissues, e.g. tumors, glands, nerves, vessels, cartilage, eyes, bone, heart, brain, nails, and skin. This provides the targets with therapeutic doses and reduces systemic side effects of the drugs. Currently-harnessed physical mechanisms for localized drug delivery include local injections, ultrasound, laser, piezoelectric materials, and electric or magnetic fields. Also, systemically-administered drug-carrying particles can be made to release their drug content in a target tissue by physical excitation (e.g. exposure to ultrasound-induced heating) of the drug carrier (Kang et al., "Drug delivery systems for intra-articular treatment of osteoarthritis", *Expert Opin Drug Deliv,* 2014). However, solutions to deliver drugs locally into all varieties of tissue (particularly in a non-destructive fashion) are limited or unavailable. For instance, drug deposition, especially into e.g. articular cartilage, bone, and nails, is challenging because of the high density and/or lack of vascularity.

There are also various methods to extract substances such as tattoos, venom, and interstitial fluid from a target. Exemplary methods are sonophoresis, microporation, and iontophoresis. Sonophoresis and microporation are still under development. The more developed iontophoresis relies on stablishing an electric current through the skin and a fluid. (Sieg et al., "Noninvasive and minimally invasive methods for transdermal glucose monitoring", *Diabetes Technol Ther,* 2005).

US 20130137951A1 and U.S. Pat. No. 8,172,790,B2 disclose needle-free injector devices adapted to inject materials through the skin without needles. In these devices, MHD actuates a piston to induce a high-pressure jet of fluid with sufficient energy to penetrate the skin causing structural modifications of the tissue. The fluid ejection lasts only a few microseconds. This limits the time of exposure to the mechanism of delivery. Furthermore, once the drug crosses the skin, it diffuses thought the circulatory system into the whole body. Accordingly, drug deposition is not localized.

US 2011/0037325 discloses integrated electro-magneto hydrodynamic micro pumps and methods for pumping fluids. The pumps of the disclosure include a flow channel adapted to contain a fluid to be pumped and a plurality of electrodes positioned adjacent to the flow channel. Voltage control means operatively associated with the plurality of electrodes applies a voltage potential to a plurality of the electrodes. A plurality of magnets is also positioned adjacent the flow channel. Magnet control means operatively associated with the plurality of magnets changes magnetic fields produced by the plurality of magnets with respect to the flow channel. The voltage control means and the magnet control means are operable to pump fluid contained in the flow channel by an electro-osmotic flow process and by a MHD flow process. Accordingly, the electrodes actuate the fluid in the whole transverse area of the channel. This configuration prevents adequate recirculation of the fluid into the channel when its aperture is obstructed. Actuation of the fluid when the channel aperture is obstructed may also cause rapid degradation of the conductive fluid, e.g. oxidation or reduction of the electrolytes, and heating. Therefore, the proper operation of this device depends on ejecting a considerable amount of the actuated fluid out of the channel. In drug delivery applications, however, if the volume of the ejected drug-carrying fluid diffuses partially into a target, a substantial fraction of the fluid would spread systemically. On the other hand, the fluid volume that can be contained in the micrometer-scale channel may be insufficient to administrate effective drug dosages to the target. Moreover, this device offers no means to orient the flow inside the body towards a target.

Accordingly, there is need for further devices for localized drug delivery as well as devices for extraction of substances from a target.

SUMMARY

The present invention is based on the observation that localized delivery of material to targets and extraction of material from targets can be achieved by exploiting the MHD phenomenon in a non-destructive fashion.

Accordingly, it is an object of the present invention to provide a device for delivering material into a target and extracting material form a target, the device comprising a frame comprising a space adapted to contain conductive fluid comprising the material, a first electrode and a second electrode positioned preferably in the space, the first electrode aligned substantially with the second electrode so that tip of the first electrode is facing tip of the second electrode, a volume V between the tip of the first electrode and the tip the second electrode, a floating current source adapted to induce an electric current through the first electrode, the conductive fluid in the volume, and the second electrode, an opening adapted to allow the material to move from the volume to the target and/or from the target to the volume, a magnet adapted to produce a magnetic field to the volume, the magnetic field being substantially perpendicular to the electric current.

According to the device of the present invention, the body of the first electrode and body of the second electrode are coated with insulating material so that only the tips of the electrodes, i.e. the transversal electrode faces, conduct electricity. The tipis of the electrodes is covered with electrically conducting, non-ferromagnetic material.

The volume V is 2000 $mm^3$ or less, in proviso that an electrode gap d defined as the mean distance of the tip of the first electrode and the tip of the second electrode is 20 mm or less. According to the Lorentz law, the directions of the electric current through the volume, the magnetic field, and the resulting Lorentz force actuating the conductive fluid in the volume are substantially perpendicular to each other.

The device may comprise means adapted to synchronize the electric current and the magnetic field so that the material is moved from the volume through the opening towards the target or from the target through the opening towards the volume according to the Lorentz force law.

According to another aspect the present invention concerns a method for delivering material into a target, the method comprising steps of providing conductive fluid comprising the material into a volume between a first electrode and a second electrode, and subjecting the conductive fluid in the volume to electric current and magnetic field, so that a magneto-hydrodynamic force is induced to the conductive fluid in the volume.

According to the method, the subjecting is to a volume of ≤2000 mm$^3$, in proviso that the first electrode is facing the second electrode and mean distance between tip of the first electrode and the tip of the second electrode is 20 mm, and that the electric current is induced through the first electrode, the conductive fluid in the volume and the second electrode, and that direction of the magneto-hydrodynamic force is substantially from the volume towards the target.

According to still another aspect, the present invention concerns a method for extracting material from a target, the method comprising providing conductive fluid comprising the material into a volume between a first electrode and a second electrode, and subjecting the conductive fluid in the volume to electric current and magnetic field, so that a magneto-hydrodynamic force is induced to the conductive fluid in the volume.

According to the method, the subjecting is to a volume of 2000 mm$^3$, in proviso that the first electrode is facing the second electrode and mean distance between tip of the first electrode and the tip of the second electrode is 20 mm, and that the electric current is induced through the first electrode, the conductive fluid in the volume and the second electrode, and that direction of the magneto-hydrodynamic force is substantially from target towards the volume.

Further objects of the present invention are described in the accompanying dependent claims.

Exemplifying and non-limiting embodiments of the invention, both as to constructions and to methods of operation, together with additional objects and advantages thereof, are best understood from the following description of specific exemplifying embodiments when read in connection with the accompanying drawings.

The verbs "to comprise" and "to include" are used in this document as open limitations that neither exclude nor require the existence of un-recited features. The features recited in the accompanied depending claims are mutually freely combinable unless otherwise explicitly stated. Furthermore, it is to be understood that the use of "a" or "an", i.e. a singular form, throughout this document does not exclude a plurality.

DESCRIPTION

Figure 1:
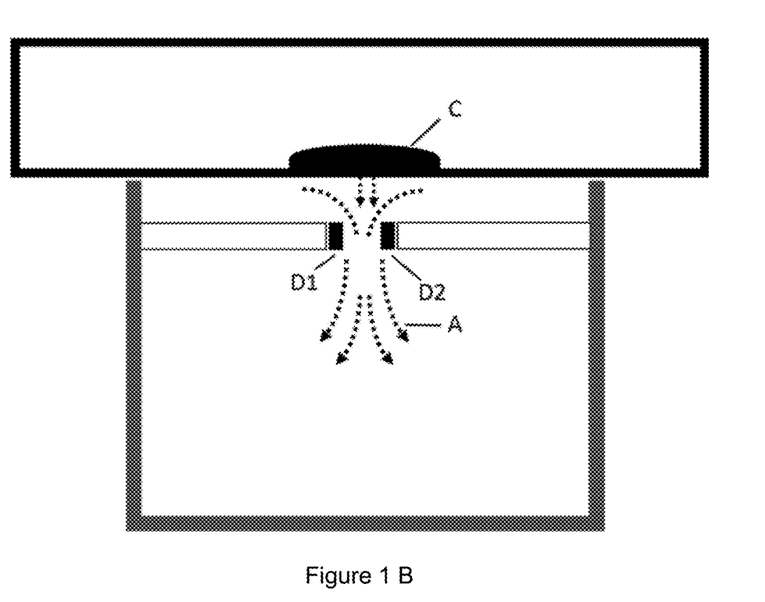
FIG. 1A illustrates the principle of the device according to the present invention for delivering material to a target, and exemplary electrode configurations.
FIG. 1B illustrates the principle of the device according to the present invention for extracting material from a target, and exemplary electrode configurations.
Figure 1A:
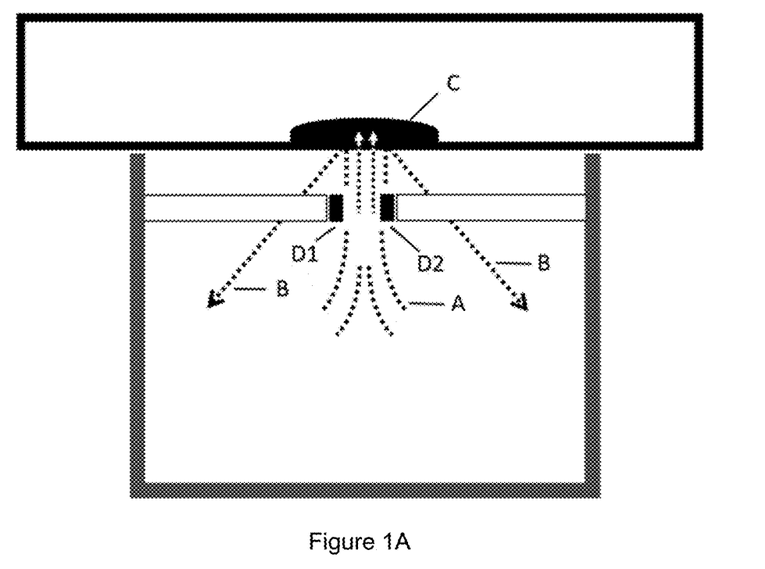

The principle of the device according to the present invention is shown in FIGS. 1A, and 1B.

When MHD produces a stream of material-carrying fluid A towards the target, most of the fluid B rebounds and remains in the frame and can be actuated again. A small fraction of the actuated material-carrying fluid C diffuses into the target. References D1 and D2 illustrate the electrodes. When the target is porous, a substantial amount of this fluid may return to the device while the material remains in the target because of e.g. its larger molecular size and/or weight.

When MHD actuates the conductive fluid in opposite direction, e.g. from the target towards the volume, drop of pressure close to the target is generated, which allows sucking out the material to the space when the opening of the device is in contact with the target. The principle is shown in FIG. 1B.

Accordingly, the device of the present invention is suitable for delivering material into a target and/or for extracting material form a target. An exemplary device 100 shown in FIG. 2A comprises a frame 101 comprising a space 102 adapted to contain conductive fluid. The fluid may comprise material to be deposited into a target, a first electrode 103A and a second electrode 103B positioned in the space, the first electrode facing the second electrode, a volume V 104 between tips of the electrodes 103a and 103b, i.e. between the transversal faces of the electrodes in the space 102.

a floating current source 105 adapted to induce a current through the first electrode, the conductive fluid in the volume, and the second electrode, an opening 106 adapted to allow the material to move from the volume to the target and/or from the target to the volume, a magnet 107 adapted to produce a magnetic field in the volume, the magnetic field being perpendicular to the current. Orientation of the magnet in figures is only for illustrative purposes.

Body of the first electrode 109A, and body of the second electrode 109B, is coated with electrically insulating material so that only the tip of the first electrode and the tip of the second electrode, i.e. the transversal faces of the electrodes conduct electricity. Exemplary insulating materials are rubber-line polymers and plastics.

The tip of the electrodes 103a, and 103b i.e. the transversal face of the electrodes, is coated with material that is electrically conductive and non-ferromagnetic, and preferably also highly resistant to corrosion and oxidation. Exemplary suitable materials are noble metals and their mixtures. Preferable noble metals are platinum and gold. High resistant to corrosion and oxidation is preferably in particular for medicinal applications.

Proper coating makes the electrodes chemically and magnetically suitable for the application while minimizing their cost. It also allows establishing a high current density in a well-defined current path.

According to the device, the volume V, i.e. the path for electric current between the electrodes, is 2000 mm$^3$ or less, in proviso that the length of electrode gap d, i.e. the mean distance of the tips of the electrodes, is 20 mm of less. This is to maintain low electric impedance, high current density, and good localization of the MHD effect for delivery or extraction. Actuation of the fluid in a proportionally small section of the frame allows convenient recirculation of the actuated fluid into the frame and reduces power dissipation and heating.

The areas of the transversal faces of the aligned electrodes, i.e. the areas coated with inert material are preferably the same. According to this embodiment the volume V is defined as the electric current path between the electrodes, and can be estimated by the equation $V=[(A1+A2)/2] \cdot d$; wherein A1 is area of transversal face of the first electrode, A2 is area of transversal face of the second electrode, and d is the mean distance between the tip of the first electrode and the tip of the second electrode.

According to the device of the present invention, it is essential that the tips of the electrodes are substantially aligned and facing each other, but they do not need to be aligned as in FIG. 2A. Exemplary electrode configurations wherein the tips of the electrodes are facing each other are shown in FIG. 2B. Accordingly, there must be a path for an electric current between tips of the electrodes. The path, i.e. the volume V is shown in FIG. 2B in grey color. The arrows indicate the electric current through the volume.

According to a preferable embodiment the device comprises means 108 adapted to synchronize the electric current and the magnetic field so that the material is moved from the volume through the opening 106 towards the target or from the target through the opening towards the volume. This is done by commuting the direction of the electric current and magnetic field at the same frequency. The frequency of the electric current can be set e.g. from the control panel of the floating current source. The direction of the magnetic field can be commuted at the frequency of the electric current by e.g. rotating the magnet, or establishing a similar frequency in the source of energy of an electromagnet. The resulting force ($\vec{f}$) is perpendicular to both the direction of the electric current through the fluid in the volume and the direction of the magnetic field according to the Lorentz force law, described by the equation: $\vec{f}=\vec{J}\times\vec{B}$, where $\vec{J}$ is the current density, $\vec{B}$ is the magnetic field, and × indicates cross product.

The electrodes are preferably at the center of the frame and in proximity to the opening to effectively move the conductive fluid and the material through the opening. According to a preferable embodiment, the distance between the electrodes and the opening is between 0 and 5 mm. The electrodes can alternatively be adapted to be in contact or partially inside the target or e.g. an adjacent tissue of the target. The area of the opening is preferably between 10 mm$^2$ and 2500 mm$^2$.

According to one embodiment the opening comprises a membrane. The membrane may be permeable or semi permeable.

According to a preferable embodiment the target is a tissue. As defined herein, tissue is any kind of biological material including eye, brain, bone, articular cartilage, nail, meniscus, ligaments, tendons, muscles, tumors, nerves, skin, individual cells, plants, and wood.

According to another preferable embodiment, the target is a non-biological material, such as ceramics, metals, stones, oil derived products, glasses, and active pharmaceutical ingredients.

The material may be a chemical or biological substance, tissue engineering constructs or their mixtures. Exemplary materials are drug molecules, cells, and viruses, bisphosphonates, steroids, proteoglycan, collagen, growth factors and drug carries (e.g. micro/nano-capsules, micro-nano-bubbles, micro/nano-rods, micro/nano-particles or micro/nano-fibers). Biologically active substances include analgesics, antagonists, anti-inflammatory agents, anthelmintics, antianginal agents, antiarrhythmic agents, antibiotics (including penicillins), anticholesterols, anticoagulants, anticonvulsants, antidepressants, antidiabetic agents, antiepileptics, antigonadotropins, antihistamines, antihypertensive agents, antimuscarinic agents, antimycobacterial agents, antineoplastic agents, antipsychotic agents, immunosuppressants, antithyroid agents, antiviral agents, antifungal agents, anxiolytic sedatives (hypnotics and neuroleptics), astringents, beta-adrenoceptor is blocking agents, blood products and substitutes, anti-cancer agents, cardiacinotropic agents, contrast media, corticosterioids, cough suppressants (expectorants and mucolytics), diuretics, dopaminergics (antiparkinsonian agents), haemostatics, immunosuppressive and immunoactive agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, vasidilators, neuron blocking agents, anticholinergic and cholinomimetic agents, antimuscarinic and muscarinic agents, vitamins, and xanthines.

Preferred exemplary drugs for localized deposition with MHD are drugs targeting dense and/or avascular tissue (e.g. articular cartilage, bone and nails), and drugs susceptible to interact with other drugs or to produce adverse systemic side effects such as anticancer and osteoarthritis drugs (e.g., chemotherapy agents and growth factors). Preferred are also drugs that are constructed from precursors e.g. insulin. The MHD method, can also be used to deliver e.g., amphiphilic gels, liposomes, polyelectrolyte capsules, nanodiscs, microemulsions, and lipid particles that self-assemble inside the tissue to form complex functional structures. The MHD method may also serve to deliver contrast agents into tissue for high-resolution imaging.

According to a particular embodiment, the target is nail and the material is an antifungal agent.

According to another particular embodiment, the target is a tumor and the material is a chemotherapeutic agent.

According to another particular embodiment, the target is skin and the material is collagen or collagen fibers, microfibers or nanofibers.

According to another particular embodiment, the target is articular cartilage and the material is a drug for treating osteoarthritis, rheumatoid arthritis or articular cartilage injury.

According to another particular embodiment, the target is bone and the material is an anti-osteoporotic agent.

According to another particular embodiment, the target is an eye and the material is a drug to treat glaucoma or intraocular hypertension.

According to another particular embodiment, the target is the pancreas, and the material is a precursor to a drug to manage or treat e.g. diabetes.

According to another particular embodiment, the targets are cells (e.g. the cells in a plant leaf) and the material consist of particles of a heavy metal coated with plasmid DNA.

The conductive fluid is either a liquid, an ionized gas, or combination of two or more liquids or ionized gases that conduct electricity. The conductive fluid is preferably an electrolytic solution and most preferably a hypertonic saline solution providing low electric impedance. The electric impedance of the conductive fluid is preferably below 500Ω and most preferably below 50Ω to prevent power dissipation and heating.

As defined herein, drug delivery or deposition is an active transportation of a drug from an initial site to a localized tissue or structure where its effect is desired. The terms delivery and deposition underscore the importance of increasing the retention time, slower 'wash out', of the drug from the targeted site. Localized drug delivery is of interest on the development of therapies for e.g. cancer, osteoarthritis, rheumatoid arthritis, osteoporosis, connective tissue injury (such as articular cartilage, meniscus or discus), intraocular pressure, vocal fold paralysis, heart diseases, fungal infections, and skin diseases or skin rejuvenation.

Figure 3:
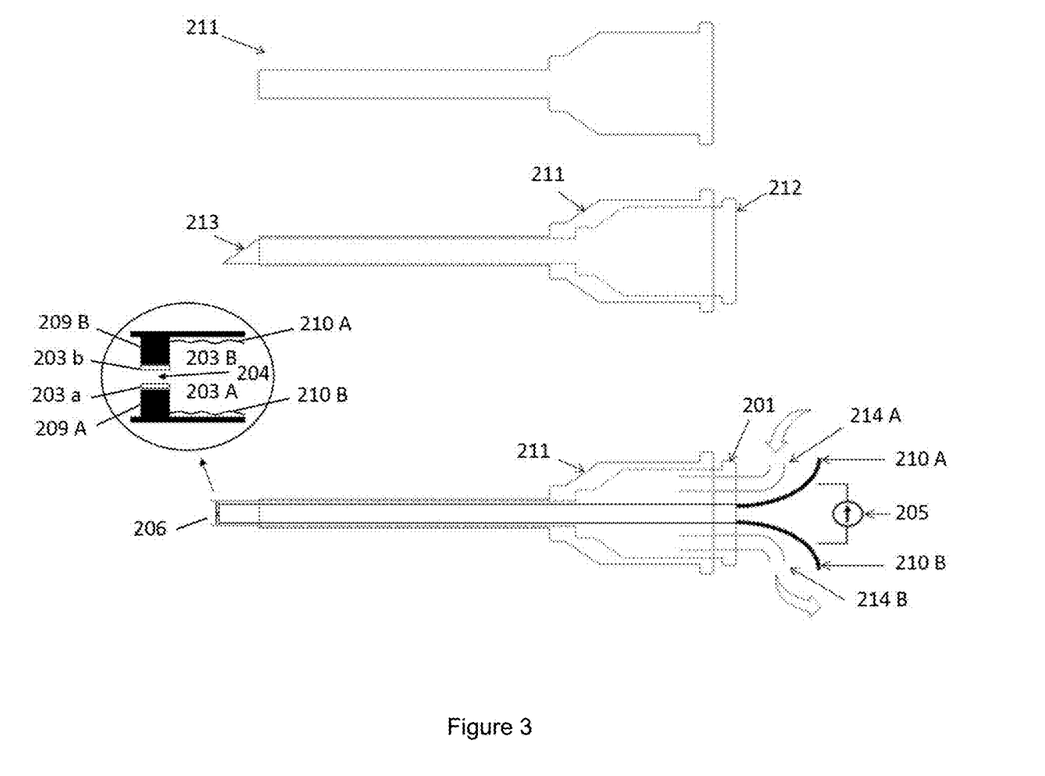
FIG. 3 illustrates a non-limiting exemplary device according to the present invention for localized drug delivery.
Figure 5:
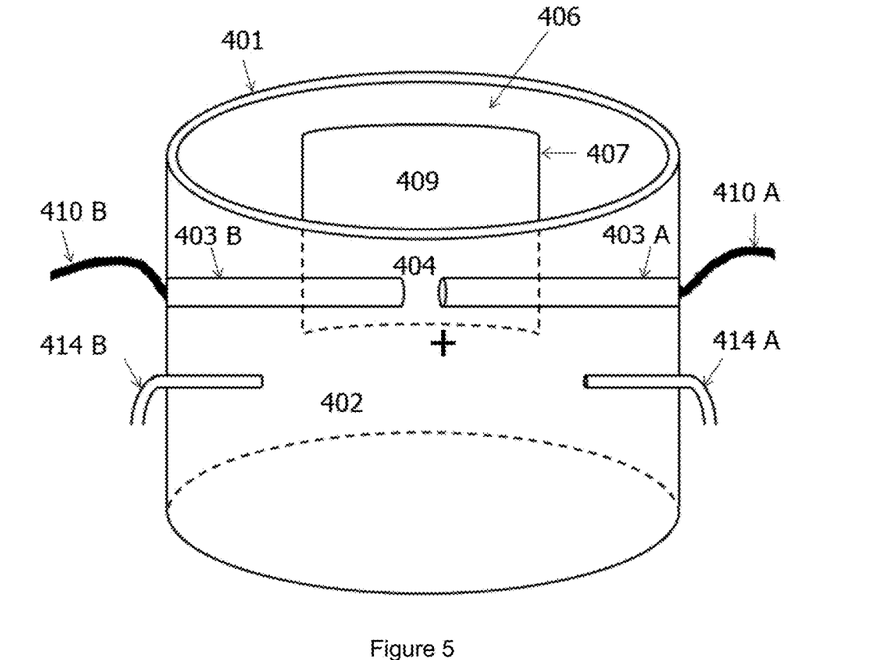
FIG. 5 illustrates a non-limiting exemplary device according to the present invention for deposition or extraction of molecules or particles into or from targets such as skin, eyes, wood, and plants.

The device of the present invention includes a frame. Exemplary frames are a catheter and a chamber. Exemplary devices comprising a catheter and a chamber as a frame are shown in FIGS. 3 and 5, respectively. The frame includes a space for the conductive fluid and the material. Exemplary suitable spaces are a reservoir, a removable cartridge, and one or more channels.

The device includes at least a pair of electrodes, i.e. the first electrode and the second electrode. The electrodes are preferably copper electrodes, and the tip of the electrodes is coated with e.g. platinum, gold or other noble metal resistant to corrosion and oxidation. These metals are unsusceptible to interactions with magnetic fields since they are non-ferromagnetic. Platinum is a preferred metal, since it is highly resistant to corrosion and oxidation, which prevents the addition of electrolysis residues. The electrode body is coated with an insulating material. This makes the electrodes chemically and magnetically suitable for the application while minimizing their cost. It also allows establishing a high current density in a well-defined current path, i.e. the volume V. According to an exemplary embodiment the electrodes are held at their position by the electrode bodies, 109A, 109B made of copper isolated with a polymeric film such as polyurethane. A pair of insulated wires 110A, 110B connect the electrodes through the electrode bodies to the terminals of a floating current source.

According to one embodiment, the first electrode 103A and the second electrode 103B are located within the space 102. When the space and thus also the volume 104 comprises the conductive fluid, the electrodes are in physical contact with the fluid.

The first electrode faces the second electrode, and a gap d between the electrode tips is 20 mm or less, more preferably 10 mm or less, most preferably 5 mm or less. An exemplary range of electrode gap is 0.01 mm and 5 mm. Accordingly, when the electrodes are positioned as disclosed, an electric current can be induced effectively through the electrodes and the conductive fluid in the volume.

The floating current source, as defined herein, is any source of electric power capable of establishing an electric current through the electrodes and the fluid in the volume. Exemplary current sources are a voltage source, rechargeable batteries, and an electromagnetically-induced electric field.

The device shown in FIG. 2A includes a magnet 107 for generating a magnetic field to the conductive fluid in the volume. The magnetic field may be generated by one or more permanent magnets or electromagnets, and in both cases, the field can be static or dynamic. The magnetic field can be dynamic, e.g. generated by AC current. Also, the magnet or electromagnet can be rotating around the volume. The intensity of the magnetic field is preferably between 0.1 and 12 T. The magnet may be located within the frame or outside the frame. According to one embodiment, the magnetic field is generated by an external magnetic resonance imaging (MRI) scanner. This permits localized delivery of drugs under imaging guidance. When the procedure is carried out under MRI image guidance, gadolinium or other contrast agents may be added to the conductive fluid to provide feedback of the deposition drug, such as location and concentration in the targeted tissue.

The preferred electric current is either DC or AC depending on whether the magnetic field is static or dynamic, respectively. According to an embodiment, the current is alternating current (AC). AC refers to all waveforms, unipolar or bipolar, except direct current. Exemplary waveforms of the AC current are pulsed, saw tooth, square, and sinusoidal.

It is known that a parasitic capacitance exists between the electrodes. Thus, if the current is AC, its frequency is preferably below 1 kHz and most preferably below 100 Hz to minimize capacitive losses. The root mean square (RMS) value for the electric current, synchronized with the magnetic field, is preferably below 500 mA and most preferably below 400 mA. For safety reasons, the maximum output voltage of the current source is preferably limited to a maximum value of 40 V.

An exemplary device according to the present invention for drug administration in a body is shown in FIG. 3. The device includes a frame in the form of a catheter 201 comprising a pair of electrodes 203A, 203B. In a procedure resembling a peripheral blood-vessel cannulation, a hollow cannula 211 covering a needle 212 is introduced into the body through the skin. The tip 213 of the needle is preferably sharp to facilitate skin penetration. Once the cannula is placed, the needle is removed. Then, the device is threaded through the cannula to the vicinity of the targeted tissue.

The device shown in FIG. 3 includes a pair of copper electrodes 203A, 203B coupled to the catheter by the electrode bodies 209A, 209B made of copper isolated with a polymer film, such as polyurethane. The electrode tips 203a, 203b conduct electricity. The electrodes are located in the proximity of the opening 206. A pair of wires 210A, 210B connect the electrodes through the electrode bodies to the terminals of a floating current source 205. The catheter comprises a space, for conductive fluid comprising the material, in the form of a pair of tubes 214A, 214B. A conductive fluid, such as a saline solution carrying drugs, can be flushed to the space and thus also to the volume by pumping it in via the tube 214A and sucking it out via the tube 214B or vice versa. The flushing provides thermal control and also prevents both accumulation of electrolysis residue and degradation of the solution, e.g. chemical reduction or oxidation of the electrolytes.

Once a current is established through the fluid, a magnetic field applied externally causes the MHD effect. The current source 205 is synchronized with the magnetic field to maximize the Lorentz force along the desired direction, e.g. towards the targeted tissue. After administering the drug, both the catheter and the cannula are removed.

By customizing the size of the catheter, the device can be used in combination with commercial devices such as laparoscopic trocars, sheaths for cardiac catheterization, and vessel cannulas. For instance, the electrodes can be micromachined needles.

As localized drug deposition into tissue is achieved by the Lorentz force and the associated MHD phenomenon, the efficacy of the procedure is independent of the length and thickness of the catheter. Accordingly, a strong jet through the catheter is unnecessary. Consequently, this method is effective even if elements with large hydrodynamic resistance are used, e.g. a long and thin catheter or a micro needle.

A variant of the device shown in FIG. 3 includes a strong permanent magnet generating the required magnetic field in a direction perpendicular to the flow of electric current through the saline solution.

According to one embodiment, the conductive fluid does not include the material. The presence of the material in the conductive fluid is not needed, when a solution containing the material is first injected in-situ e.g. to the intra-articular space and then a device according to the present invention is used to deposit the material from the intra-articular space into the targeted tissue, e.g. cartilage by MHD. Also, when the device is for extracting material from the target, the conductive fluid does not include the material prior to extracting.

Figure 2:
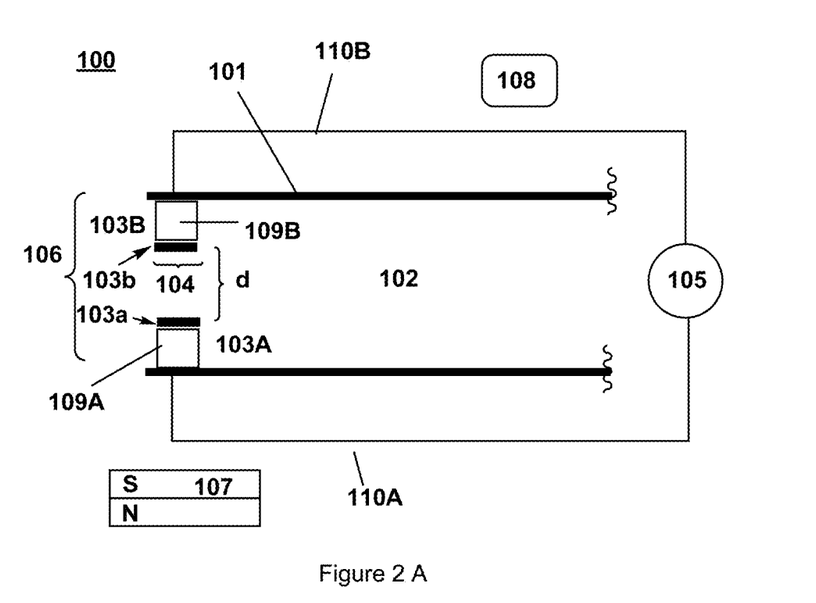
FIG. 2A illustrates a schematic view of a non-limiting exemplary device according the present invention.
FIG. 2B illustrates exemplary non-limiting electrode configurations of the device according to the present invention, wherein the grey area represents the volume, and the arrows indicate the electric current through the volume.
Figure 4:
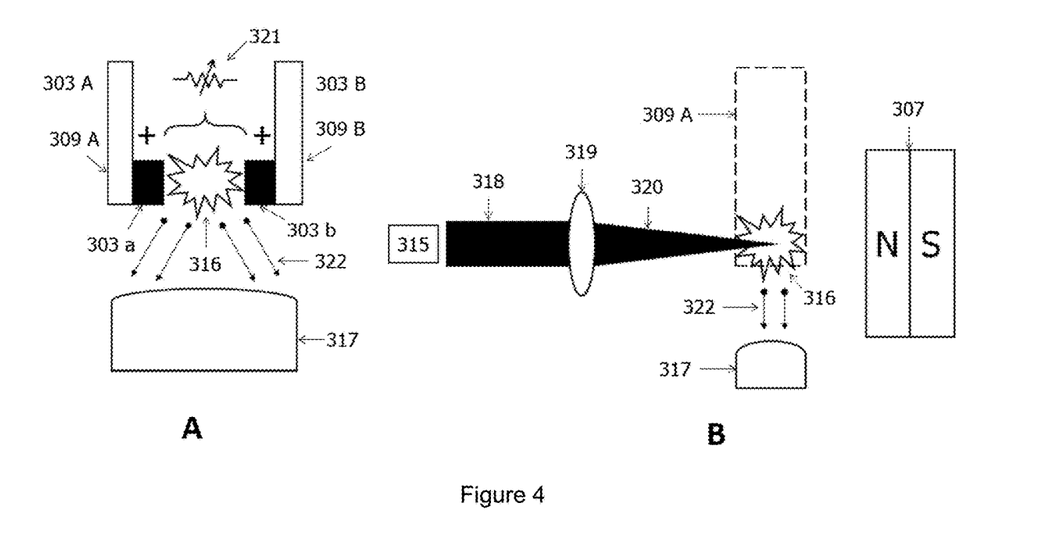
FIG. 4 illustrates a non-limiting exemplary device according to the present invention comprising laser beam generating means adapted to induce optical breakdown of a conductive fluid (A front view; B side view)

In another embodiment, the MHD device such as that of FIG. 2 is combined with a laser pulse generating means 315 configured to provide plasma sparks 316 produced by laser-induced optical breakdown of the conductive fluid, which enhances the efficacy of localized delivery of drugs into tissue as shown in FIG. 4. It also permits the use of the MHD phenomenon in non-conducting or low-conducting fluids using low voltage, e.g. low power dissipation. Furthermore, the use of a laser emitter permits generating high-pressure fluid jets into very confined spaces. According to this embodiment, the electrodes 303A, 303B are placed close to the target 317 and are immersed in a conductive fluid with the material. By establishing an electric current between the electrodes, an external magnetic field initiates the MHD phenomenon. The magnetic field is generated either by a permanent magnet or an electromagnet 307. Then, a laser beam 318 is focused at the electrode gap by e.g. a lens 319. Intense pulses of focused light 320 cause a breakdown of the medium, e.g. saline solution. Thus, each light pulse creates a plasma spark, which provides a low impedance path 321 for the electric current. The lifespan of each plasma spark is preferably femtoseconds to microseconds. During this time, an intense and spatially confined electric current is obtained through the low impedance path provided by the plasma channel. Since the Lorentz force actuating the solution is proportional to the electric current, high pressure jets 322 of the solution are directed towards the targeted tissue during each light pulse. The sparks also generate ultrasonic shockwaves which enhance the efficacy of the drug delivery (Pitt et al., "Ultrasonic drug delivery—a general review", *Expert Opin Drug Deliv*, 2004; Nieminen et al., "The Potential Utility of High-Intensity Ultrasound to Treat Osteoarthritis", *Osteoarthritis Cartilage*, 2014; Nieminen et al., "Delivering agents locally into articular cartilage by intense MHz ultrasound", *Ultrasound Med Biol*, 2015). The repetition frequency of the light pulses can range from Hz to THz. The method may rely on an unrestricted number of light pulses or exposure time. The laser pulse energy is preferably higher than 100 mJ. The electrode gap must be such that the plasma sparks significantly reduce the electric impedance between the electrodes. Exemplary electrode gap ranges from 100 μm to 5 mm.

An exemplary device suitable to deliver substances into the external parts of the body e.g. skin, nails, or eyes, and to extract from skin or other tissue is shown in FIG. 5. The device comprises a frame in the form of a chamber 401 encompassing a pair of tubes, 414A, 414B a permanent magnet or electromagnet 407, and a pair of electrodes 403A, 403B made of e.g. graphite separated by a distance d. The area of the electrode tips and the distance between them determine the volume 404 where the conducting fluid is subjected to the MHD. The electrodes are plugged to an external floating current source through a pair of wires 410A, 410B. To deliver and/or extract material, the device is placed over the targeted tissue in such a manner that the chamber opening 406 faces the tissue. The chamber is then filled with a conductive fluid through one of the tubes. Alternatively, a prefilled chamber is used or a cartridge containing the fluid is placed in the frame. Once a current is passed through the electrodes, the Lorentz force pushes the fluid either towards the tissue, e.g. to deposit material into the target, or towards the bottom of the chamber to extract material from the target. The direction of the Lorentz force depends on the directions of both the electric current and magnetic field. The root mean square (RMS) value for the electric current, synchronized with the magnetic field, is preferably below 500 mA and most preferably below 400 mA. For safety reasons, the maximum output voltage of the current source is preferably limited to 40 V. The intensity of the magnetic field is preferably between 0.1 and 12 T. The electric impedance of the saline solution is preferably below 500 and most preferably below 50 to prevent power dissipation and heating. A sustained flux of solution through tubes 414A, 414B prevents heating, accumulation of residues from electrolysis, and degradation of the conductive solution. The electrode gap is typically 20 mm or less, preferably between 0.01 and 10 mm, more preferably between 0.01 and 5 mm. The electrode diameter is preferably between 1 and 10 mm. Other variants of this device may comprise two or more magnets or electromagnets arranged either inside or outside the chamber. Applications of this device include but are not limited to delivery of drugs into the skin to treat e.g. warts or hypertrophic scars, delivery of collagen or collagen fibers into the skin for skin rejuvenation, delivery of drugs into the eyes, delivery of ink molecules into the skin to make tattoos, delivery of particles of a heavy metal coated with plasmid DNA into cells, and suction of substances from the skin to e.g. remove tattoos or venom and to extract interstitial fluid for non-invasive glucose monitoring. By delivering collagen fibers or microfibers, disrupted tissue, e.g. articular cartilage, may be rehabilitated or reconstructed. Furthermore, to remove tattoos or other molecules from the skin, a washing effect can be achieved by iteratively delivering pure saline solution into the skin and then extracting it. This can be done by commuting the direction of either the electric current or magnetic field.

Figure 6:
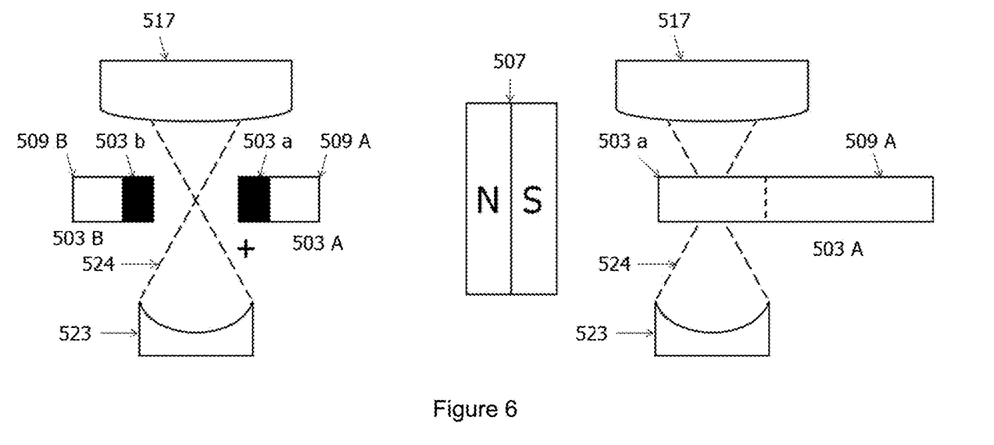
FIG. 6 illustrates a non-limiting exemplary device according to the present invention comprising means for generating focused ultrasound.

Exemplary ultrasound generating means for the device according to the present invention is shown in FIG. 6. According to this embodiment, the MHD phenomenon is enhanced with ultrasound (US). US provides a mechanism to increase the MHD efficiency by actuating bubbles produced by electrolysis (e.g., displacing the bubbles) and by removing residue from the electrodes. This helps to maintain low electric impedance between the electrodes which consequently reduces power dissipation and thus heating. The US also provides a means to increase the delivery rate of molecules into tissue (Nieminen et al., "The Potential Utility of High-Intensity Ultrasound to Treat Osteoarthritis", *Osteoarthritis Cartilage*, 2014). The method entails pointing an ultrasound source, such as e.g. a focused ultrasound transducer 523, towards the target such as a tissue 517, so that the focus of the US beam is close to both the targeted tissue and the volume i.e. in the distance d between the electrode tips 503*a*, 503*b*. The electrodes are attached to the frame through the electrode bodies 509A, 509B made of e.g. of copper isolated with a polymer film, such as polyurethane. The focused US beam 524 actuates the electrolysis bubble by e.g. cavitation and streaming, and enhances the delivery of molecules into tissue by e.g. producing microstreaming/jetting and radiation forces towards the target. These mechanisms for actuating the material can serve to modulate the concentration of material in the actuated volume, e.g. near tissue interface. Ultrasound can also be used to actuate the porous structure of the tissue. The frequency of the ultrasound is preferably kHz to MHz. The intensity of the US beam at the focal point is preferably between mW/cm$^2$ and kW/cm$^2$.

Figure 7:
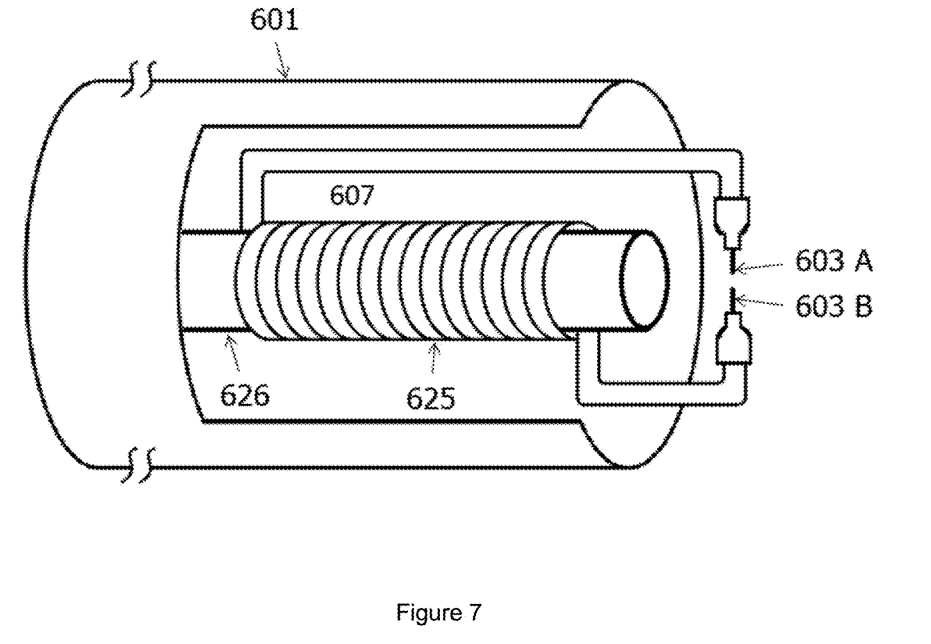
FIG. 7 illustrates a non-limiting exemplary device according to the present invention encompassing a coil for generating a magnetic field and means for generating an electric current.

According to another embodiment shown in FIG. 7, the frame 601 of the device comprises a magnet 607 comprising coil or micro-coil of insulated copper 625 over a ferromagnetic core 626, and a pair of electrodes 603A, 603B tips of which are coated with e.g. platinum. Each electrode is plugged to a different end of the coil. An external power source in the near-field (e.g. inductively coupled) can induce an electric current in the coil which in turn produces a magnetic field. The frequency of the resonant energy coupling is preferably between kHz and MHz. The distance d between the electrode tips is preferably between 0.001 and 5 mm. The electrode diameter is preferably between 0.01 and 3 mm. The intensity of the magnetic field is preferably between 0.1 and 5 T. This device permits avoiding the use of an external current source and magnets or electromagnets. Complementarily, this device may include analog or digital electronic circuits to e.g. store energy and control the intensity, frequency and waveform of the current. By reducing, e.g. electronically dividing, the frequency of the electric current, capacitive losses due to parasitic capacitances between the electrodes are reduced. This increases the efficiency of the device and thus reduces power dissipation and thus heating. The root mean square (RMS) value for the electric current, synchronized with the magnetic field, is preferably below 500 mA and most preferably below 400 mA. For safety reasons, the maximum output voltage of the current source is preferably limited to 40 V. The electric impedance of the saline solution is preferably below 500Ω and most preferably below 50Ω to prevent power dissipation and heating.

Figure 8:
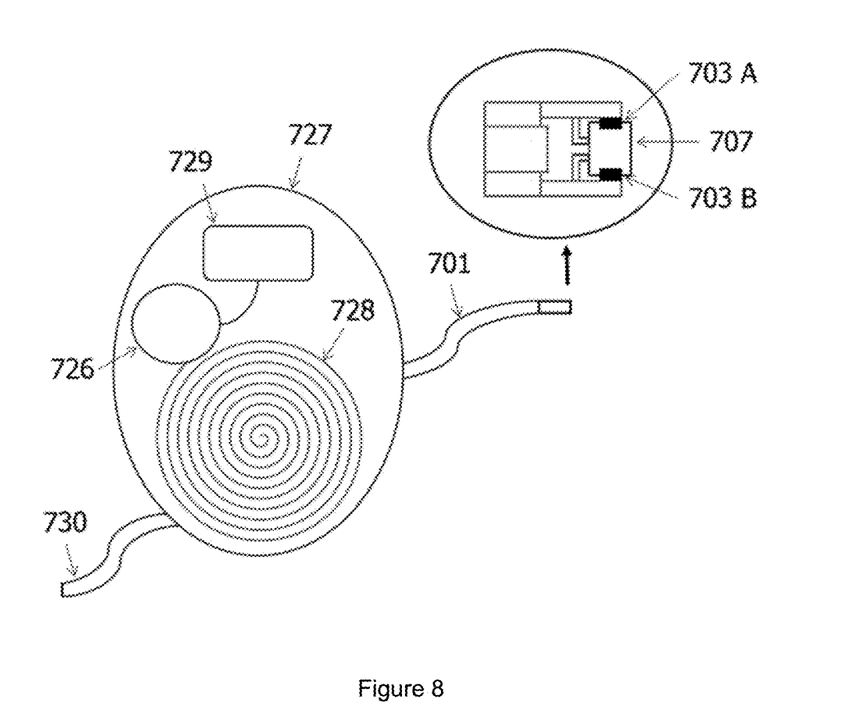
FIG. 8 illustrates a non-limiting exemplary implantable device according to the present invention for long-term localized delivery/administration of drugs inside the body.

In another embodiment of the invention, shown in FIG. 8, the device is implantable and suitable for long-term drug delivery/administration. The device comprises a catheter 701 integrating a pair of electrodes 703A, 703B and a permanent magnet 707, a refillable reservoir 727 to contain a conductive fluid such as saline solution carrying drugs, a rechargeable battery 726, an antenna 728, an electronic circuit 729 to control the operation of the device, and a tubing 730 to refill the chamber. The reservoir is made of e.g. titanium. The catheters are made of e.g. polyethylene. These materials are bio- and MRI-compatible. The catheter tip for drug delivery encompasses two electrodes of e.g. copper coated with e.g. platinum, and one permanent magnet arranged to create a magnetic field which is perpendicular to the electric current in the electrode gap. The device can be implanted into the body close to a targeted tissue. The catheter for drug delivery is then fixed in such a manner that a Lorentz force is produced towards the target. One end of the tubing for refilling the chamber remains outside the body. The antenna serves to recharge the battery wirelessly through near-field inductive coupling with an external power supply. The electronic circuit controls the current through the electrodes to administer the drug in a pre-programmed fashion or according to commands transmitted wirelessly by extracorporeal instruments through the antenna 728. The distance between the electrodes is preferably between 0.001 and 5 mm. The electrode diameter is preferably between 0.01 and 3 mm. The root mean square (RMS) value for the electric current, synchronized with the magnetic field, is preferably below 500 mA and most preferably below 400 mA. For safety reasons, the maximum output voltage of the current source is preferably limited to 40 V. The intensity of the magnetic field is preferably between 0.1 and 5 T. The electric impedance of the saline solution is preferably below 500Ω and most preferably below 50Ω to prevent power dissipation and heating. The device may also integrate sensors and transmit data wirelessly from those sensors to extracorporeal instruments. Alternatively, the chamber can encompass several reservoirs so that different drugs can be delivered. Alternatively, the electrodes can be micro-needles of silicon, silicon dioxide, silicon nitride, gold or platinum. This can have applications on drug delivery or improve electrode anchoring into the brain and heart. The use of micro-needles may also find applications in single cell treatment and analysis. In another variant of this embodiment, the data transmission may rely on other physical means such as e.g. optics, magnetism, and ultrasound.

Figure 9:
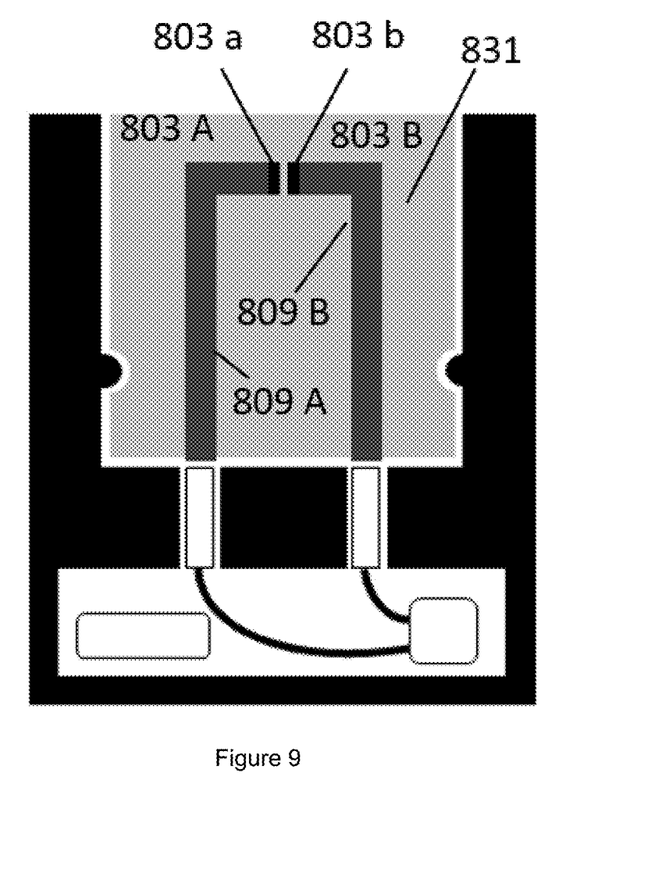
FIG. 9 illustrates a non-limiting exemplary device according to the present invention comprising a removable cartridge for containing conductive fluid.

According to another embodiment shown in FIG. 9, the fluid is placed into the frame in a removable cartridge 831. The cartridge is adapted to fit into the frame and preferably also adapted to provide space to the electrodes 803A, 803B.

According to one embodiment the device according to the present invention is suitable for restricting the therapeutic effect of drugs to a highly localized tissue. This relies on in-situ self-assembling or cross-linking of at least two chemical compounds, as in the case of catalytic homopolymerization of epoxy resins or building of e.g. insulin through its precursors. As an initial steep, a saline solution is charged with a first drug or chemical compound that is then delivered into the targeted tissue with MHD. Then, the residual drug-carrying solution in the vicinity of the target is disseminated from the zone either by waiting for passive dissemination or by actively circulating saline solution through the MHD device to produce a washing effect. Then, a second chemical compound is delivered by MHD. These steps may be repeated according to the number of chemical compounds to be mixed. This method provides a solution to enable the use of drugs with severe systemic side effects such as e.g. chemotherapy agents. It also provides a solution to the task of gluing from inside out e.g. anchoring, sealing. The procedure depicted by the method can be performed under image guidance. This helps to e.g. start and stop the MHD delivery based on visual monitoring of the process.

Figure 10:
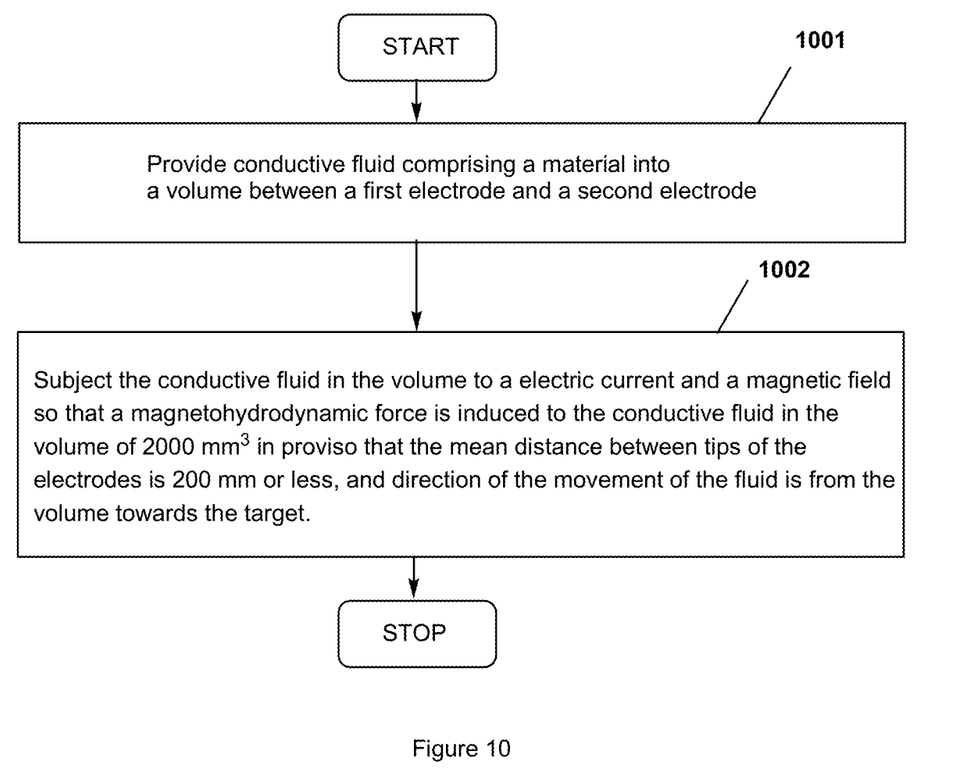
FIG. 10 shows a flow chart of a method according to an exemplifying and non-limiting embodiment of the invention for delivering material to a target.

FIG. 10 shows a flowchart of a method according to an exemplifying and non-limiting embodiment of the invention for delivering material to the target. The method comprises the following actions:
- action 1001: providing conductive fluid comprising the material into a volume between a first electrode and a second electrode,
- action 1002: subjecting the conductive fluid in the volume to electric current and magnetic field.

The subjecting to the electric current and to the magnetic field is carried out so that a magneto-hydrodynamic force is induced to the conductive fluid in the volume between the first electrode and the second electrode, and the direction of MHD force is towards the target. According to the method, the volume is ≤2000 mm$^3$, in proviso that mean distance between tip of the first electrode and the tip of the second electrode is ≤20 mm.

Figure 11:
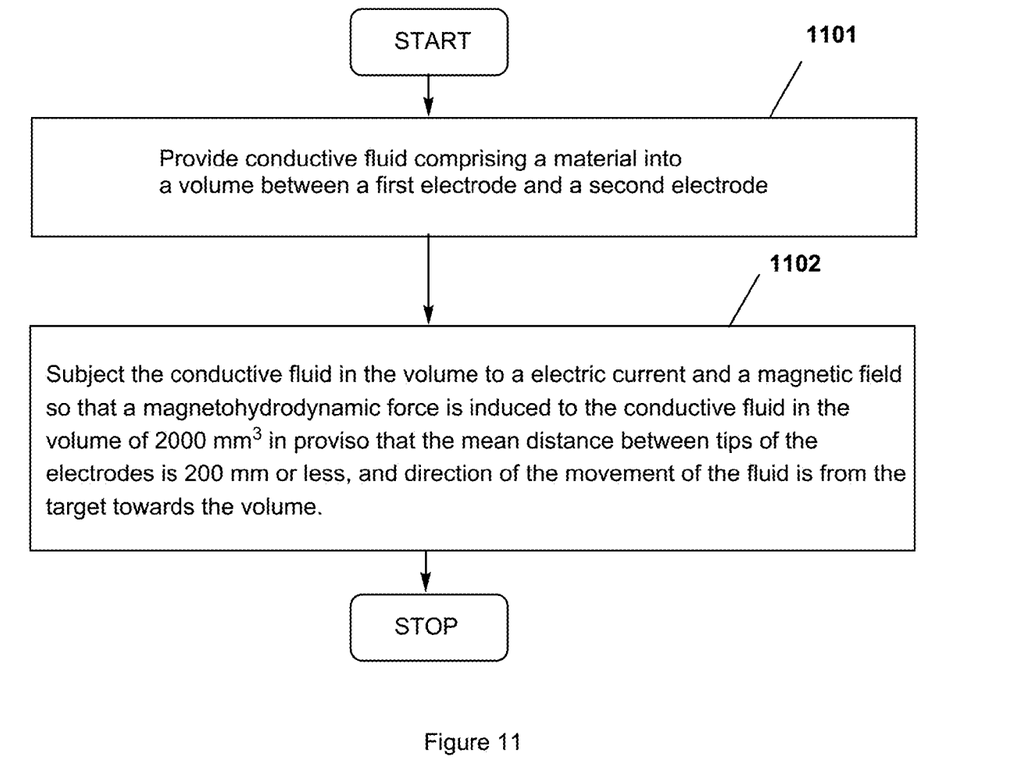
FIG. 11 shows a flow chart of a method according to an exemplifying and non-limiting embodiment of the invention for extracting material from a target.

FIG. 11 shows a flowchart of a method according to an exemplifying and non-limiting embodiment of the invention for extracting material from a target. The method comprises the following actions:
- action 1101: providing conductive fluid into a volume between a first electrode and a second electrode,
- action 1102: subjecting the conductive fluid in the volume to electric current and magnetic field.

The subjecting to the electric current and to the magnetic field is carried out so that a magneto-hydrodynamic force is induced to the conductive fluid in the volume between the first electrode and the second electrode, and the direction of MHD force is from the target. According to the method, the volume is ≤2000 mm$^3$, in proviso that mean distance between tip of the first electrode and the tip of the second electrode is ≤20 mm.

The methods described herein can be performed by using the device according to the present invention. When the method is for delivering material into a target, the device is positioned so that the opening is towards the target and the electric current and the magnetic field are synchronized so that the MHD effect is from the volume to the target. When the method is for extracting material from a target, the device is positioned so that the opening is in contact with the target and the electric current and the magnetic field are synchronized so that the MHD effect is from the target to the volume, then, low pressure near the target results from streaming of the fluid in opposite direction to the target. The drop in low pressure is explained by the Bernoulli's principle and fluid dynamics.

EXAMPLES

Example 1

Delivery of Phosphotungstic Acid (PTA) into Bovine Articular Cartilage

Control: bovine articular cartilage was immersed in 1% PTA (~2.8 kDa) in phosphate buffered saline (PBS) for 40 s.

Treatment: bovine articular cartilage was immersed in PTA 1% in PBS and exposed to MHD for 40 s. The MHD method applied graphite cylindrical electrodes (ø=6 mm), 3 mm electrode gap, and 400 mA.

Figure 12:
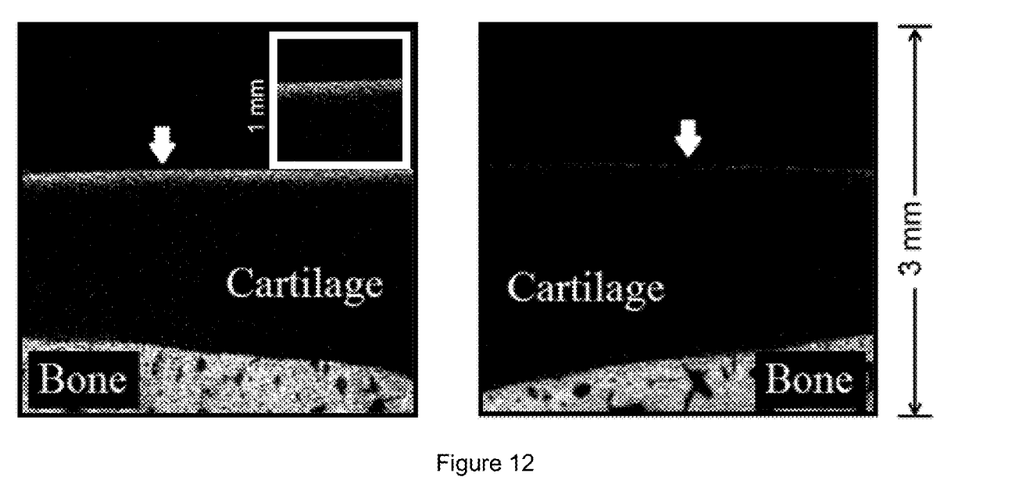
FIG. 12 illustrates delivery of phosphotungstic acid (ca. 2.8 kDa) 1% in phosphate buffered saline into bovine articular cartilage using the device according to the present invention (left treatment; right control), and FIG. 13 Illustrates delivery of methylene blue 0.01% in phosphate buffered saline 1% into human nails in vitro.

Results are shown in FIG. 12. The figure shows two slices (treatment/left and control/right) of 150 µm comprising cartilage and subchondral bone imaged with X-ray microtomography (XMT). The treated sample shows enhanced diffusion of PTA as compared to the control.

Example 2

In-Vitro Delivery of Methylene Blue (MB) into Human Nails In Vitro

Control: Fingernail was immersed in a solution of MB (0.01%) in PBS (1%) for 10 minutes.

Treatment; Fingernail was immersed in the MB solution and exposed to MHD during 10 minutes. The MHD method applied graphite cylindrical electrodes (ø=6 mm), 3 mm electrode gap, and 400 mA.

Figure 13:
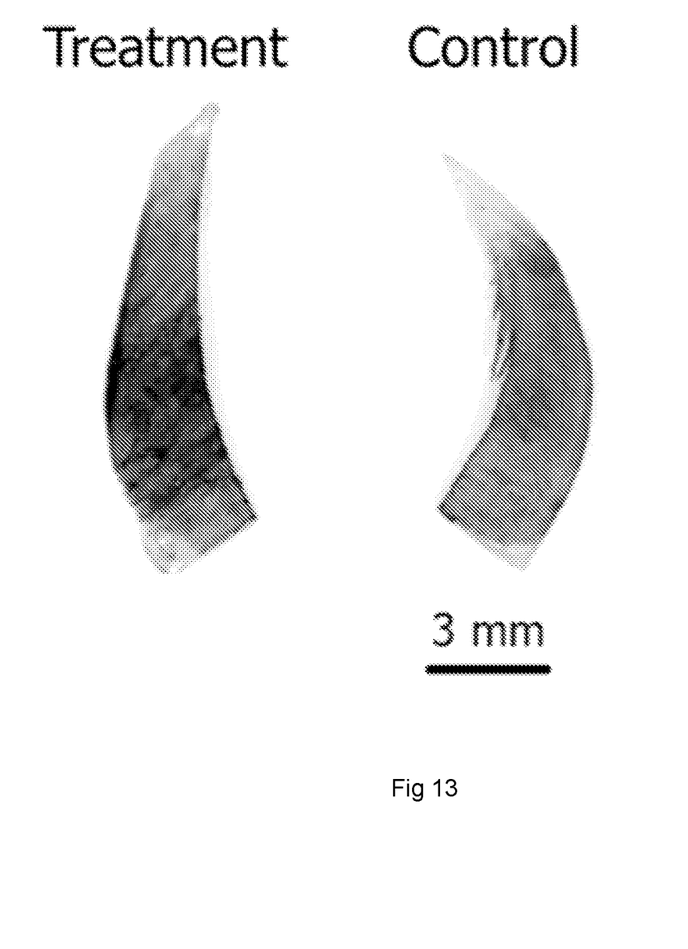

Results are shown in FIG. 13. The figure shows a photograph of two samples of human finger nail (treatment/left and control/right). The darkest regions correspond to the largest concentration of MB. Diffusion of MB into the treated sample is stronger than in the control.

Further embodiments of the present invention are disclosed in the following numbered clauses.

1. A method for delivering material into a target, the method comprising steps of
   a) providing a device comprising
      a frame comprising a space adapted to contain conductive fluid comprising the material,
      a first electrode and a second electrode positioned preferably in the space, the first electrode substantially aligned with the second electrode so that tip of the first electrode is facing tip of the second electrode
      a volume V between the tip of the first electrode and the tip the second electrode,
      a floating current source adapted to induce an electric current through the first electrode, the conductive fluid in the volume, and the second electrode,
      an opening adapted to allow the material to move from the volume to the target and/or from the target to the volume,
      a magnet adapted to produce a magnetic field to the volume, the magnetic field being substantially perpendicular to the electric current,
      wherein only the tips of the electrodes conduct electricity, and wherein the volume is 2000 mm$^3$ or less, in proviso that the electrode gap d defined as the mean distance of the tip of the first electrode and tip of the second electrode is 20 mm or less,
   b) providing a conductive fluid comprising the material into the volume,
   c) positioning the device so that the opening is towards the target, and
   d) subjecting the conductive fluid comprising the material to magnetic field and electric current so that moving of the conductive fluid comprising the material is directed towards the target.

2. The method according to clause 1, the method further comprising subjecting the fluid to an ultrasound beam and/or to a laser beam.

3. The method according to clause 1 or 2, wherein electric impedance of the conductive fluid is below 500Ω.

4. The method according to any of clauses 1-3, wherein root mean square of intensity of the electric current is ≤500 mA.

5. The method according to any of clauses 1-4, wherein the magnetic field is at least 0.1 T.

6. The method according to any of clauses 1-5, wherein the magnetic field is generated by a MRI instrument.

7. The method according to any of clauses 1-6, wherein the material is selected from drugs, collagens, chemotherapeutic agents, contrast agents, tissue engineering constructs, micro- and nanofibers, drug carriers, DNA carries, and inks.

8. The method according to any of clauses 1-7, wherein the target is a tissue, preferably selected from skin, nail, eye, bone, brain, tumors, hear, vocal folds, cartilage, wood, or plants.

9. A method for extracting material from a target, the method comprising
   a) providing a device comprising
      a frame comprising a space adapted to contain conductive fluid comprising the material,
      a first electrode and a second electrode positioned preferably in the space, the first electrode aligned with the second electrode so that tip of the first electrode is facing tip of the second electrode
      a volume V between tip of the first electrode and tip the second electrode,
      a floating current source adapted to induce an electric current through the first electrode, the conductive fluid in the volume, and the second electrode,
      an opening adapted to allow the material to move from the volume to the target and/or from the target to the volume,
      a magnet adapted to produce a magnetic field to the volume, the magnetic field being perpendicular to the electric current,
   wherein only the tips of the electrodes, conduct electricity, and wherein the volume is 2000 mm$^3$ or less, in proviso that the electrode gap (d) defined as the mean distance of the tip of the first electrode and tip of the second electrode is 20 mm or less,
   b) providing a conductive fluid into the volume,
   c) positioning the device so that to that the opening is in contact with the target, and
   d) the subjecting the conductive fluid to magnetic field and electric current so that moving of the conductive fluid is directed from the target towards the volume.

10. The method according to clause 9, wherein electric impedance of the conductive fluid is below 500Ω

11. The method according clause 9 or 10, wherein root mean square of intensity of the electric current is ≤500 mA.

12. The method according to any of clauses 9-11, wherein the magnetic field is at least 0.1 T.

13. The method according to any of clauses 9-12, wherein the magnetic field is generated by a MRI instrument.

14. The method according to any of clauses 9-13, wherein the material is selected from ink, interstitial fluid, and venom.

15. The method according to any of clauses 9-14, wherein the target is a tissue, preferably skin.

16. A method for delivering material into a target, the method comprising steps of
   a) providing a device according to any of claims 1-15,
   b) providing a conductive fluid comprising the material into the volume of the device,
   c) positioning the device so that the opening is towards the target,
   d) subjecting the conductive fluid comprising the material to magnetic field and electric current produced by the device, and
   e) synchronizing the magnetic field and the electric current so that moving of the conductive fluid comprising the material is directed from the volume towards the target.

17. A method for extracting material from the target, the method comprising steps of
   a) providing a device according to any of claims 1-15,
   b) providing a conductive fluid into the volume of the device,
   c) positioning the device so that the opening is towards the target,
   d) subjecting the conductive fluid comprising the material to magnetic field and electric current produced by the device, and
   e) synchronizing the magnetic field and electric current so that moving of the conductive fluid is directed from the target towards the volume.

The specific examples provided in the description given above should not be construed as limiting the scope and/or the applicability of the appended claims.

What is claimed is:

1. A device for at least one of delivering material into a target and extracting material from the target, the device comprising:
   a frame comprising a space adapted to contain conductive fluid comprising the material,
   a first electrode and a second electrode protruded into the space, the first electrode aligned with the second electrode so that the tip of the first electrode is facing the tip of the second electrode,
   a volume V between the tip of the first electrode and the tip the second electrode,
   a floating current source adapted to induce an electric current through the first electrode, the conductive fluid in the volume, and the second electrode,
   an opening adapted to allow the material to move from the volume to the target and/or from the target to the volume,
   a magnet adapted to produce a magnetic field to the volume, the magnetic field being perpendicular to the electric current, wherein the volume is ≤2000 mm3,
   wherein mean distance of the tip of the first electrode and the tip of the second electrode is ≤20 mm,
   and wherein body of the first electrode and body of the second electrode are coated with insulating material wherein the insulating material is surrounded by the space, and the tip of the first electrode and the tip of the second electrode are coated with electrically conducting, non-ferromagnetic material so that only the tip of the firstelectrode and the tip of the second electrode conduct electricity.

2. The device according to claim 1, wherein the electrically conducting, non-ferromagnetic material is a noble metal.

3. The device according to claim 1, the device comprising means adapted to synchronize the electric current and the magnetic field so that the material is adapted to move from the volume through the opening towards the target or from the target through the opening towards the volume.

4. The device according to claim 1, wherein distance of the opening from the first electrode and the second electrode is from 0 to 5 mm.

5. The device according to claim 1, wherein the opening comprises a membrane permeable or semipermeable to the material.

6. The device according to claim 1, wherein the magnet is within the frame.

7. The device according to claim 1, wherein the magnet is located outside the frame.

8. The device according to claim 3, wherein intensity of magnetic field generated by the magnet is 0.1-12 T, root mean square for the electric current synchronized with the magnetic field is below 500 mA, and maximum output voltage of the floating current source is 40 V or less.

* * * * *

UNITED STATES PATENT AND TRADEMARK OFFICE
CERTIFICATE OF CORRECTION

PATENT NO. : 11,052,245 B2  
APPLICATION NO. : 15/748657  
DATED : July 6, 2021  
INVENTOR(S) : Alejandro Garcia Perez Page 1 of 1

It is certified that error appears in the above-identified patent and that said Letters Patent is hereby corrected as shown below:

On the Title Page

Item (73) please correct the assignee information from:  
HELSINGIN YLIOPISTO  
To:  
GLUCOMODICUM OY.

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*